United States Patent [19]
Williams et al.

[11] Patent Number: 5,563,809
[45] Date of Patent: Oct. 8, 1996

[54] MEASUREMENT/CONTROL OF SHEET MATERIAL USING AT LEAST ONE SENSOR ARRAY

[75] Inventors: Paul Williams, Columbus; Tom Domin, Galena; Eugene S. Green, Columbus; Roger A. Holmes, Dublin, all of Ohio

[73] Assignee: ABB Industrial Systems, Inc., Columbus, Ohio

[21] Appl. No.: 223,702

[22] Filed: Apr. 6, 1994

[51] Int. Cl.⁶ .................................................. G06F 19/00
[52] U.S. Cl. ............... 364/560; 364/469.01; 364/471.03
[58] Field of Search ..................................... 364/560, 471, 364/473, 468, 469; 162/259, 263; 356/429, 430, 431; 73/159, 73–77; 250/559.01, 559.03, 559.04, 559.05, 559.06, 559.07, 559.08, 559.1, 559.11, 559, 15, 559.19, 559.20, 559.34, 559.46, 559.48

[56] References Cited

U.S. PATENT DOCUMENTS

| | | | |
|---|---|---|---|
| 3,562,500 | 2/1971 | Grant | 235/151.3 |
| 3,695,532 | 10/1972 | Lindstaedt | 242/55 |
| 3,695,539 | 10/1972 | Lindstaedt | 242/58.6 |
| 3,837,593 | 9/1974 | Dörfel | 242/66 |
| 3,936,665 | 2/1976 | Donoghue | 162/252 |
| 4,098,641 | 7/1978 | Casey et al. | 162/198 |
| 4,947,684 | 8/1990 | Balakrishnan | 73/159 |
| 4,950,911 | 8/1990 | Williams et al. | 250/563 |
| 4,954,891 | 9/1990 | Burk et al. | 358/101 |
| 4,980,846 | 12/1990 | Chapman | 364/550 |
| 5,071,514 | 12/1991 | Francis | 162/259 |
| 5,122,963 | 6/1992 | Chen | 364/471 |
| 5,269,883 | 12/1993 | Beuther | 162/198 |
| 5,298,122 | 3/1994 | Munch et al. | 162/259 |

OTHER PUBLICATIONS

Brochure–ReelView™ 900, Copyright 1993 by ABB Process Automation Inc.

Primary Examiner—James P. Trammell
Attorney, Agent, or Firm—Killworth, Gottman, Hagan & Schaeff

[57] ABSTRACT

A paper web is monitored for measurement and manufacturing control by a stationary web sensor extending across the entire web which is raster scanned by the motion of the web. Massive amounts of data are processed by a look up table memory addressed by digitized sensor data and the output from a reference memory containing element specific information. The lookup table is loaded with data to define a characteristic or property of the web corresponding to digitized sensor data interpreted in view of element specific data from the reference memory. Rapidly processed data is stored in a memory in a form facilitating its display and interpretation by an operator of the web manufacturing machine and also control of the machine. By controlling operation of the machine, uniformity of the web is substantially improved and, by taking the measurements closely adjacent the initial processing end of the web, corrections of nonuniformity in the web are quickly effected. To measure and control absolute characteristics and properties of the web, a second, preferably stationary, sensor adjacent the finished end of the web monitors the web adjacent a takeup reel. Alternately, for basis weight measurement and control, the weight of the takeup reel is monitored and combined with the web width and machine operating speed to determine an absolute web basis weight. Thus, uniformity of the web and absolute values of characteristics and properties of the web can be measured and controlled.

26 Claims, 6 Drawing Sheets

| 11-5 A/D (DEC) | Gray Scale (HEX) | 10-5 A/D (DEC) | Gray Scale (HEX) | 10-4 A/D (DEC) | Gray Scale (HEX) | Event Data (HEX) | (BIN) |
|---|---|---|---|---|---|---|---|
| 0-79 | 0 | 0-79 | 0 | 0-63 | 0 | E | (1110B) |
| 80  | 0 | 80  | 0 | 64  | 0 | D | (1101B) |
| 86  | 1 | 85  | 1 | 70  | 1 |   |         |
| 92  | 2 | 90  | 2 | 76  | 2 |   |         |
| 98  | 3 | 95  | 3 | 82  | 3 |   |         |
| 104 | 4 | 100 | 4 | 88  | 4 | F | (1111B) |
| 110 | 5 | 105 | 5 | 94  | 5 |   |         |
| 116 | 6 | 110 | 6 | 100 | 6 |   |         |
| 122 | 7 | 115 | 7 | 106 | 7 |   |         |
| 128 | 8 | 120 | 8 | 112 | 8 |   |         |
| 134 | 9 | 125 | 9 | 118 | 9 |   |         |
| 140 | A | 130 | A | 124 | A |   |         |
| 146 | B | 135 | B | 130 | B |   |         |
| 152 | C | 140 | C | 136 | C | B | (1011B) |
| 158 | D | 145 | D | 142 | D |   |         |
| 164 | E | 150 | E | 148 | E |   |         |
| 170 | F | 155 | F | 154 | F |   |         |
| 176 | F | 160 | F | 160 | F | 7 | (0111B) |

MEASUREMENT/CONTROL OF SHEET MATERIAL USING AT LEAST ONE SENSOR ARRAY

BACKGROUND OF THE INVENTION

The present invention relates in general to measuring and controlling at least one characteristic of a web of sheet material as the web is being manufactured and, more particularly, to methods and apparatus for measuring and controlling a web of sheet material as it is being manufactured by means of a first sensor, preferably a stationary sensor, to maintain the uniformity of the web and a second sensor, also preferably a stationary sensor, to maintain the absolute value of at least one characteristic of the web. While the present invention is generally applicable to measuring and controlling the manufacture of a number of different types of web material, it will be described herein with reference to webs of paper for which it is particularly applicable and is initially being applied.

A variety of sensors have been utilized to measure and control the manufacture of sheet material which is manufactured as continuous webs moving at high speeds in the manufacturing process. The web material can be, for example, metal, plastic or, for the description of the present application, paper.

The most common and currently popular form of paper web sensor is generally moved across the web of paper in what is referred to as a cross direction (CD) scan of the web. As the sensor, for example a beta gauge basis weight sensor, is scanned across a paper web in the cross direction, the paper is moving rapidly through the paper making machine. Accordingly, the sensor detects the basis weight of a zig-zag pattern on the web in the direction of web movement or machine direction (MD). With scan speeds ranging from 100 to 400 millimeters (mm) per second, scanner instrument measuring zones ranging from 10 to 30 mm and web speeds ranging from 3 to 30 meters per second, less than 1% of the web is measured using such scanned gauges.

Separation of web property variability into cross direction and machine direction causes and effects is difficult and time consuming due to the limited machine direction measurement frequency resulting from the zig-zag scan pattern and the limited amount of the web which is actually sensed. In addition, typically five to ten CD scans must be completed before sensor results can be determined, possibly a time period of up to 30 or more minutes. Added to the delay necessitated by multiple scans, sensor scanners are normally located close to the take-up reel for the machine which results in additional delay for the paper to leave the headbox, traverse the machine and arrive at the sensor. This web travel delay is added to the time required before the effects of any corrective measures can begin to be evaluated.

In an attempt to speed up web measurement and control, a stationary optical sensor extending continuously across a paper web is disclosed in U.S. Pat. No. 5,071,514. As disclosed in the '514 patent, the stationary optical sensor must be calibrated for controlling the machine making the paper web. Calibration may be performed by a closely associated scanning optical sensor which senses discrete regions of the web as it is scanned across the web.

The noted stationary and scanning optical sensors are positioned at the wet end of the paper making machine and are supplemented by scanning sensors located at the dry end of the paper making machine. Data from the scanning sensors at the dry end of the paper making machine may be correlated with the stationary optical sensor for ultimate control of the paper making machine. Unfortunately, in the system of the '514 patent, the calibration performed by the wet end scanning optical sensor is not entirely accurate such that calibration effectively must be delayed until correlation of the dry end scanning sensors with the stationary optical sensor located at the wet end of the machine.

A second stationary optical sensor is disclosed in U.S. Pat. No. 4,950,911 for performing inspection of a sheet of material to detect flaws which occur within the sheet of material. In this system, threshold levels are adapted on a pixel by pixel basis in response to raw data coming in from the stationary optical sensor. Event signals are generated for pixel signals which pass through the threshold levels with the event signals being used to identify flaws in the sheet of material which is being inspected. While the system of the '911 patent is very effective for detecting flaws in sheets of material, the system is limited in terms of speed and therefor data collection rates. Further, no provision is made for controlling the machine making the sheet material in response to data generated by the inspection system.

There is thus a need for an improved arrangement for monitoring webs of sheet material for accurate determination of sheet characteristics and use of those characteristics to rapidly control the machine making the webs. Preferably, the monitoring arrangement will be able to collect data for statistical analysis of the material and the process making the material. Also the monitoring arrangement would monitor the sheet material near the initial processing of the material, i.e. near the wet end of a paper making machine, and be able to independently control the uniformity of the webs of sheet material. If characteristics of the sheet material are to be absolutely controlled, they would be controlled from a second sensor, preferably a stationary sensor, monitoring the web near the final processing of the sheet material.

SUMMARY OF THE INVENTION

This need is met by the methods and apparatus of the present invention wherein a web of sheet material is monitored for measurement and control of one of more characteristics or properties of the web during manufacture. Preferably, a stationary web sensor extends across the entire cross direction (CD) of the web such that the entire web can be monitored. For example, if one or more line scan cameras are used to monitor a line of points, elements or pixels across the entire web, the camera output signals can be read at a rate synchronized to the motion of the web as it is manufactured to effect a raster scanning of the web. In any event, the sensor generates massive amounts of data which are processed by a look up table memory which is addressed by digitized sensor data and the output from a reference memory which maintains point, element or pixel specific information for the characteristic or property being sensed.

The lookup table is loaded with data such that its readout defines a characteristic or property of the web which is determined by the digitized sensor data interpreted in view of the pixel specific data contained within the reference memory. This rapid processing of massive amounts of data is stored in a memory bank in a form which facilitates its display and therefor its interpretation by an operator of a machine producing the web of material for measurement or monitoring the web and also for control of the machine. By controlling operation of the machine producing the web, uniformity of the web is substantially improved and, by taking the measurements closely adjacent the initial processing of the web, corrections of nonuniformity in the web are quickly and accurately made.

Since measurements taken proximate the initial processing of the web of material can not represent the finished web product, to measure and control absolute characteristics and properties of the web, a second sensor is provided adjacent the finished web. The sensor may be a second stationary sensor which monitors the web adjacent a web takeup or collection reel. Alternately, for basis weight measurement and control, the weight of the collection reel is monitored and combined with the web width and machine operating speed to determine an absolute basis weight for the web. Thus, uniformity of the web and absolute values of characteristics and properties of the web can be measured and controlled by the invention of the present application.

In accordance with one aspect of the present invention, a method for measuring at least one physical property of sheet material comprises the steps of: monitoring the sheet material at a location substantially adjacent to initial processing thereof; generating a signal representing the sheet material adjacent to initial processing thereof; converting the signal into digital signals having magnitudes representing monitored corresponding points on the sheet material; addressing a reference memory in synchronism with the corresponding points on the sheet material to access point specific information for the corresponding points; and, addressing a lookup table with the digital signals and the point specific information to retrieve physical property information for the sheet material corresponding to the digital signals from the lookup table.

Preferably, the step of monitoring the sheet material at a location substantially adjacent to initial processing thereof is performed across the entire width of the sheet material. The method may further comprise the steps of: storing the physical property information in a memory; processing the physical property information stored in the memory to generate image signals; and, displaying the image signals.

The method may still further comprise the steps of: passing the physical property information to a controller for controlling manufacture of the sheet material to maintain uniformity of the sheet material; monitoring the sheet material at a location substantially adjacent to final processing of the sheet material to generate sheet signals representative of a given characteristic of the sheet material; and, controlling the machine in response to the sheet signals to further control the absolute value of the given characteristic of the sheet material. The given characteristic may comprise basis weight. If so, the step of monitoring the sheet material at a location substantially adjacent to final processing of the sheet material may comprise the step of monitoring the weight of the sheet material as it accumulates.

In accordance with another aspect of the present invention, a method for measuring at least one physical property of sheet material comprises the steps of: receiving electromagnetic radiation representative of the sheet material therefrom at a location substantially adjacent to initial processing of the sheet material; generating a signal representing the electromagnetic radiation received from the sheet material; converting the signal into digital signals having magnitudes representing the intensity of electromagnetic radiation received from corresponding points on the sheet material; addressing a reference memory in synchronism with the corresponding points on the sheet material to access point specific information for the corresponding points; and, addressing a lookup table with the digital signals and the point specific information to retrieve physical property information for the sheet material corresponding to the digital signals from the lookup table.

Preferably, the step of receiving electromagnetic radiation representative of the sheet material therefrom is performed across the entire width of the sheet material. The method may further comprise the steps of: storing the physical property information in a memory; processing the physical property information stored in the memory to generate image signals; and, displaying the image signals.

For one form of data storage, the physical property information comprises n bit digital gray scale values and the step of storing the physical property information in memory comprises the steps of: truncating n lower order bits of each memory address to define spatial zones $2^n$ bits wide addressed by resulting truncated memory addresses; substituting the digital gray scale values for the truncated n lower order bits to form $2^n$ data structure addresses for each of the truncated memory addresses; addressing the memory with the histogram addresses; reading each memory location addressed by the histogram addresses; incrementing the value read from each memory location addressed by the histogram addresses; and, storing the incremented value into each memory location addressed by the histogram addresses. Accordingly, statistical analyses, graphical representations for example by histograms, and the like are facilitated.

In accordance with yet another aspect of the present invention, a system for controlling a machine making a product in the form of a moving web of sheet material comprises a stationary web sensor extending across the entire width of the web of sheet material for monitoring the web of sheet material and generating web signals representative of the web of sheet material. A controller responsive solely to the web signals is provided for controlling the machine to maintain uniformity in the web of sheet material.

In accordance with still another aspect of the present invention, a system for controlling a machine making a product in the form of a moving web of sheet material comprises a scanning web sensor adapted for movement across the entire width of the web of sheet material for monitoring the web of sheet material and generating web signals representative of the web of sheet material, the scanning web sensor comprising a linear array of sensor elements aligned transverse to the web of sheet material. A controller responsive to the web signals is provided for controlling the machine to maintain uniformity in the web of sheet material.

In accordance with a further aspect of the present invention, a system for controlling a machine making a product in the form of a moving web of sheet material comprises a stationary web sensor comprising at least two linear arrays of sensor elements extending across at least two portions of the web of sheet material for monitoring the at least two portions of the web of sheet material and generating web signals representative of the at least two portions of the web of sheet material. A controller responsive to the web signals is provided for controlling the machine to maintain uniformity of the web of sheet material.

In accordance with yet still another aspect of the present invention, a system for controlling a machine making a product in the form of a moving web of sheet material comprises a first stationary web sensor extending across the entire width of the web of sheet material for monitoring the web of sheet material and generating first web signals representative of the web of sheet material. A second stationary web sensor measures a given characteristic of the web of sheet material and generates second web signals representative of the web of sheet material. A controller responsive to the first and second web signals is provided for controlling the machine to maintain uniformity and an absolute value of the given characteristic in the web of sheet material. The second stationary web sensor may comprise reel sensing apparatus for measuring the weight of a reel accumulating the web of sheet material as it is produced.

In accordance with still a further aspect of the present invention, a method for controlling a machine making a product in the form of a web of sheet material comprises the steps of: initializing the machine to produce a web of sheet material having known characteristics satisfying requirements of a given product produced by the machine; monitoring the web of sheet material at a location substantially adjacent to initial processing of the web of sheet material; generating web signals representative of the web of sheet material; and, controlling the machine in response to the web signals to establish uniformity in the web of sheet material regardless of the absolute requirements of the given product.

The method may further comprise the steps of: monitoring the product at a location substantially adjacent to final processing of the web of sheet material to generate product signals representative of a given characteristic of the product; and, controlling the machine in response to the product signals to further control the absolute value of the given characteristic of the product. The step of monitoring the product at a location substantially adjacent to final processing of the web of sheet material may comprise the step of monitoring the weight of the product as it accumulates. Preferably, the step of monitoring the web of sheet material is performed across the entire width of the web of sheet material.

In accordance with yet still a further aspect of the present invention, a method for controlling at least one physical property of sheet material as the sheet material is being manufactured comprises the steps of positioning a first stationary sheet material sensor at a first location along the sheet material substantially adjacent to initial processing of the sheet material; operating the first stationary sheet material sensor to generate first sensor signals representative of at least one physical property of discrete elements of the sheet material at the first location; converting the first sensor signals into first digital signals having magnitudes representing the at least one physical property of the discrete elements of the sheet material at the first location; addressing a reference memory in synchronism with the discrete elements of the sheet material to access element specific information for the discrete elements; addressing a lookup table with the first digital signals and the element specific information to retrieve from the lookup table physical property information for the sheet material corresponding to the first sensor signals; and, controlling the manufacture of the sheet material in response to the physical property information to maintain uniformity of the at least one physical property of the sheet material.

The method may further comprise the steps of: positioning a second sheet material sensor at a second location along the sheet material substantially adjacent to final processing of the sheet material; operating the second sheet material sensor to generate second sensor signals representative of at least one physical property of the sheet material at the second location; and, controlling the manufacture of the sheet material in response to the second sensor signals to maintain an absolute value of the at least one physical property of the sheet material. The step of operating the second sheet material sensor to generate second sensor signals may comprise the step of monitoring the weight of the sheet material as it accumulates.

In accordance with yet still another aspect of the present invention, a system for controlling a machine making a product in the form of a moving web of sheet material comprises a first stationary web sensor extending across the entire width of the web of sheet material for receiving light therefrom and generating first web signals representative of the web of sheet material. A second stationary web sensor measures a given characteristic of the web of sheet material and generates second web signals representative of the web of sheet material. A controller responsive to the first and second web signals is provided for controlling the machine to maintain uniformity and an absolute value of the given characteristic in the web of sheet material. The second stationary web sensor may comprise weight sensing apparatus for measuring the weight of accumulating sheet material as it is produced.

In accordance with a final aspect of the present invention, a method for controlling a machine making a product in the form of a web of sheet material comprises the steps of: initializing the machine to produce a web of sheet material having known characteristics satisfying requirements of a given product produced by the machine; receiving light representative of the product from the web of sheet material at a location substantially adjacent to initial processing of the web of sheet material; generating web signals in response to the light received from the web of sheet material; and, controlling the machine in response to the web signals to establish uniformity in the web of sheet material regardless of the absolute requirements of the given product.

The method may further comprise the steps of: monitoring the product at a location substantially adjacent to final processing of the web of sheet material to generate product signals representative of a given characteristic of the product; and, controlling the machine in response to the product signals to further control the absolute value of the given characteristic of the product. The step of monitoring the product at a location substantially adjacent to final processing of the web of sheet material comprises the step of monitoring the weight of the product on a reel which accumulates the product.

It is thus an object of the present invention to provide improved methods and apparatus for monitoring webs of sheet material for measurement of one or more sheet characteristics and properties; to provide improved methods and apparatus for monitoring webs of sheet material for measurement of one or more sheet characteristics and properties, and use of those characteristics and properties to rapidly control the machine making the webs; to provide improved methods and apparatus for monitoring webs of sheet material wherein data will be collected for statistical analysis of the material and the process making the material; to provide improved methods and apparatus for monitoring webs of sheet material near the initial processing of the material to measure the uniformity of the webs of sheet material; to provide improved methods and apparatus for monitoring webs of sheet material near the initial processing of the material to measure and independently control the uniformity of the webs of sheet material; and, to provide improved methods and apparatus for monitoring webs of sheet material wherein characteristics of the sheet material are absolutely controlled by signals from a second sensor, preferably a stationary sensor, monitoring the web near the final processing of the sheet material.

Other objects and advantages of the invention will be apparent from the following description, the accompanying drawings and the appended claims.

DETAILED DESCRIPTION OF THE INVENTION

While the present invention is generally applicable to measuring and controlling the manufacture of many different types of webs of sheet material, it will be described herein with reference to webs of paper for which it is particularly applicable and is initially being applied. Further, while the invention will be described with reference to measuring and controlling the manufacture of a paper web in response to optical monitoring, it is noted that other forms of sensors can be used in the present invention. Thus, the invention is generally applicable to methods and apparatus for monitoring or processing signals which represent an interaction with or an emanation from a web of sheet material. Such signals may be the result of sensors utilizing sound, light, radiation or other currently used or later developed sensor technologies.

Figure 1:
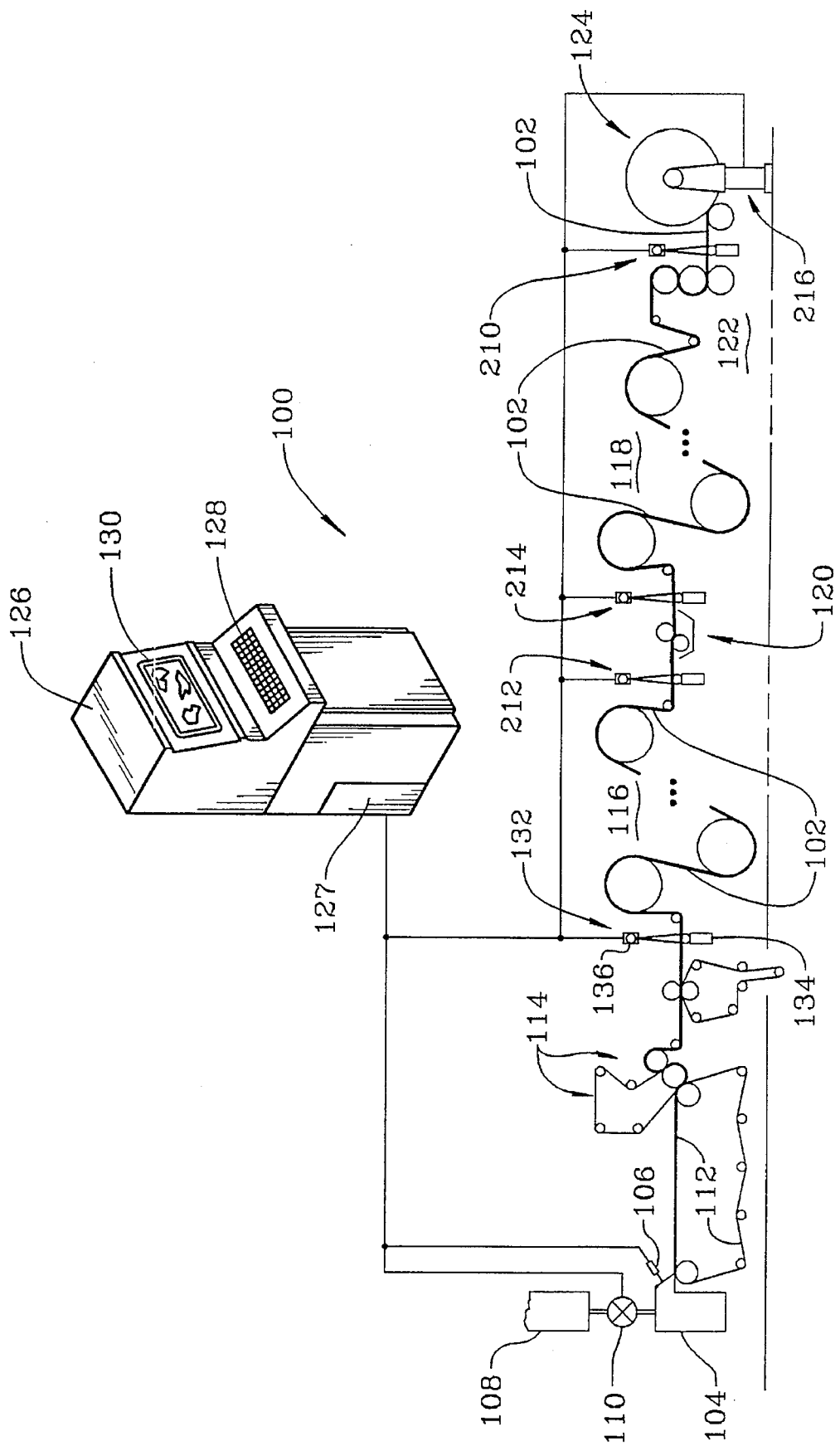
FIG. 1 is a schematic representation of a paper making machine incorporating the invention of the present application.

With reference to FIG. 1, a paper making machine 100 schematically illustrates the invention of the present application for measuring and controlling manufacture of a paper web 102. The machine 100 includes a headbox 104 which defines a headbox slice by a slice lip which is controlled along its length by a plurality of actuator cells 106. A pulp slurry of fibers suspended in water is conveyed to the headbox 104 from a supply 108 via a stock valve 110 such that the slurry can be applied to a wire 112 to form the paper web 102.

As the web 102 passes along the wire 112, excess water is drawn from the web 102 which leaves the wire 112 and passes through a wet press 114. The web 102 may be acted upon by driers 116, 118, a size press 120, a calendar stack 122 and other devices and processing stations (not shown) before being wound onto a takeup or collecting reel 124.

An operator's console 126 includes a processor system 127 for controlling the paper making machine 100 by means including the plurality of actuator cells 106, the stock valve 110, and the other devices and processing stations which are utilized along the path of the web 102 through the machine 100. The operator's console 126 includes a keyboard 128 for entry of information into and control of the processor system 127 to thereby control the machine 100 and a display 130 through which an operator of the machine 100 is advised of machine operations, machine settings and the like, and also measurements and controls in accordance with the invention of the present application.

The processor system 127 of the operator's console 126 receives web signals from at least one sensor for measuring and controlling the web 102 of material as it is being manufactured. In FIG. 1, a first web sensor preferably comprises a stationary web sensor 132 which, in the illustrated embodiment, comprises an optical sensor having a light source 134 on one side of the web 102 and a camera 136 on the opposite side of the web 102 for sensing light from the light source 134 which is transmitted through the web 102. Preferably, the light source provides light across the entire width or cross direction (CD) of the web 102 and the camera 136 comprises one or a series of cameras which can monitor the entire width of the web 102.

While light transmission is illustrated in FIG. 1, it should be noted that light may be received from the web 102 by the camera 136 either after transmission through the web 102 and/or after reflection from the web 102 dependent upon the property or properties being monitored. An example of reflective light sensing is illustrated in U.S. Pat. No. 4,950,911 which discloses a sheet inspection system and is incorporated herein by reference. In addition, while optical sensors are illustrated, other web sensors can be utilized in the invention of the present application.

Figure 2:
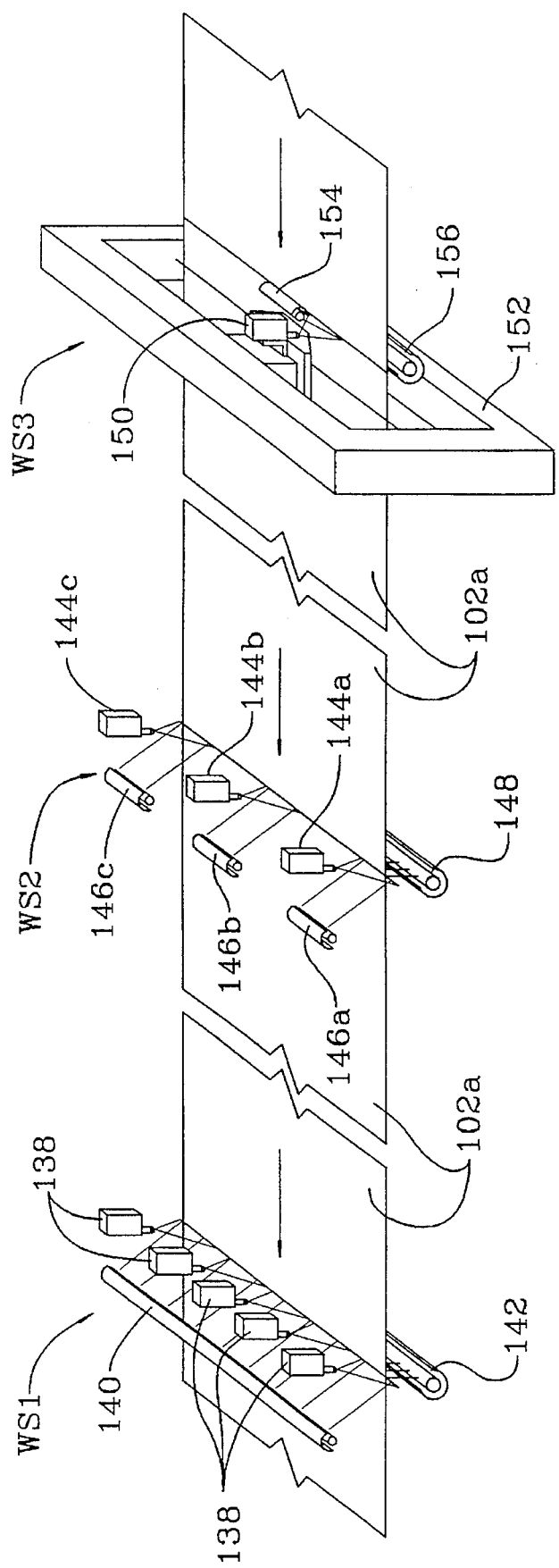
FIG. 2 is a schematic perspective representation of three different embodiments of optical web sensors for the present invention.

FIG. 2 illustrates three different embodiments of optical web sensors for the present invention. The first embodiment of an optical web sensor WS1, which extends across and monitors the entire width or CD of a web 102a, comprises a series of five (5) cameras 138 which are supported over the web 102a and provide overlapping fields of view to image the entire width or CD of the web 102a. Each of the cameras 138 comprises a linear detector array of sensor elements or an equivalent of such an array for generating image signals representative of individual elements of the web 102a. Of course, more or fewer cameras can be provided dependent, for example, upon the camera design and width of the web being monitored. The web 102a is illuminated from above by a light source 140 for reflective light sensing by the cameras 138 and/or the web 102a is illuminated from below by a light source 142 for transmissive light sensing by the cameras 138.

The second embodiment of an optical web sensor WS2, which monitors at least two portions of the web 102a, comprises three cameras 144 which monitor three portions of the web 102a as illustrated in FIG. 2: the camera 144a monitors the front of the web 102a; the camera 144b monitors the middle of the web 102a; and, the camera 144c monitors the back of the web 102c. Each of the cameras 144 comprises a linear detector array of sensor elements or an equivalent of such an array. Again, the web 102a may be illuminated from above by one or more light sources, three corresponding light sources 146a–146c being illustrated, and/or from below by a light source 148 which can extend entirely across the web 102a or be made up of two, three or more individual sources to properly illuminate the web 102a from below.

The third embodiment of an optical web sensor WS3, which monitors the entire width or CD of the web 102a, comprises a scanning web sensor. In this embodiment, a camera 150, comprising a linear detector array of sensor elements or an equivalent of such an array, is supported by a scanning frame 152 for movement back and forth across the web 102a in the cross direction (CD), i.e. transverse to the direction of movement of the web 102a. The web 102a may be illuminated from above by a light source 154 and/or from below by a light source 156 which is also carried back and forth across the web 102a by operation of the scanning frame 152. The light sources can be any of a variety of known sources including, for example, the light source illustrated in U.S. Pat. No. 4,954,891 which is incorporated herein by reference.

While any of the optical web sensor embodiments shown in FIG. 2 can be used in the invention of the present application, the first embodiment WS1 is the currently preferred embodiment and, accordingly, the invention will be described with reference to this embodiment. The method and apparatus of the present application for measuring and controlling manufacture of sheet material, a paper web, will now be described with reference to FIG. 3.

A camera controller 160 includes a camera multiplexer 162 for multiplexing line rate and data rate clocks from a timing control circuit 164 to one or more line scan cameras 166, silicon charge coupled device (CCD) cameras being used in a working embodiment of the present invention. The line scan cameras 166 are scanned in synchronism with movement of the web 102 to effect a raster scanning of the web 102. Of course, sufficiently fast or strobed raster scan cameras, i.e. cameras which have more than one line of detectors arrayed across the web 102, can be used in the present invention since the image data can be extracted from such raster scan cameras on a line-by-line basis.

The timing control circuit 164 also generates clock and line sync signals for a digital signal processor 168 from line rate and data rate echoes that are synchronized to video analog signals received from the line scan cameras 166a through 166x. The camera controller 160 also performs dc restoration for signals from the line scan cameras 166a through 166x, analog processing via an analog processor 170 and line synchronizes video signals from the line scan cameras 166a through 166x into one video signal for input to the digital signal processor 168. For example, line scan cameras often provide video signals in two channels A and B which should be independently compensated due to different electronics within the two channels.

The video signals may be provided in a one detector, i.e. one CCD, one charge injection device (CID), or one equivalent detecting cell, per measurement mode or a two detector per measurement mode, 1D/M or 2D/M. If pairs of detectors are combined, for example to prevent mismatched channels from causing a striping effect often referred to as "zebra striping", then the pairs of detectors are combined by video control circuitry 172 which also conforms the line scan camera bank timing to the RS-170 TV standard for VCR recording of line scans and interfaces a standard TV area camera or a VCR standard TV playback to the digital signal processor 168. The camera section also includes remote interface serial link circuitry 174 for interfacing with a host processor(s) 127a of the processor system 127. The camera controller 160 can be constructed from commercially available components as will be apparent to those skilled in the art and will be described further herein only to the extent necessary for understanding of the invention of the present application.

An analog-to-digital (A/D) converter 176 of the digital signal processor 168 converts analog video signals received from the camera controller 160 to digital video signals or digital point, element or pixel signals having magnitudes representing the intensity of electromagnetic radiation received from corresponding points on the web 102 of sheet material. The digital video signals are processed by a look up table memory 178 which is addressed by the digital video signals and corresponding pixel reference values stored in a reference memory 180 on a per pixel (or pixel pair) basis. The read out of the look up table memory 178 is thus a function and representative of both the digital video signals and a corresponding stored reference value.

An event and gray scale parser circuit 182 parses the functional output of the look up table memory 178 into event and level signals which, together with address (position) signals, are transmitted to a histogram circuit 184. A position logic and clocks generator 186 generates all clocks required for the digital signal processor 168 and the histogram circuit 184. The digital signal processor 168 also may "grab" a snapshot of either the raw data from the A/D converter 176 or the output data from the look up table memory 178 in a snapshot memory 188 and deliver a resulting snapshot or data set on demand to an external unit, such as the host processor(s) 127a of the processor system 127, for presentation or further processing.

The sort & pack circuits 190, 192 of histogram circuit 184 sort and pack incoming streams of event, level, and address (position) signals received from the digital signal processor 168 according to one of a number of selectable histogramming modes which will be described hereinafter. A histogram mode control circuit 194 controls mode multiplexer circuits 196, 198 and an increment or add circuit 200 to store the packed signals incrementally or additively in either of two independent histogram memory banks, bank A 202 and bank B 204. The histogram circuit 184 then delivers either of the two data sets contained in memory bank A 202 and memory bank B 204 on demand to an external unit, such as the host processor(s) 127a of the processor system 127, for presentation or further processing.

When compared to the prior art, the invention of the present application provides a clearer picture of the spatial and temporal variability of sheet properties for both rapidly and precisely measuring the web 102 as it is being manufactured and for controlling the manufacturing process. The cameras 138, employing one or more linear arrays of sensor elements, do this by forming a dynamic image of the sheet properties, using the sheet motion itself to provide raster coverage in the machine direction (MD) while electronically scanning through the one or more detector arrays in the cross machine (CD) direction.

The cameras 138 utilize one or more linear detector arrays to sense optical energy from irradiating sources in the visible and near infrared portions of the electromagnetic spectrum. The sensed source energy arrives at the cameras 138 after transmission through and/or reflection from the web 102. The intensity, spectral content, and polarization of the source energy received by each element of the one or more linear arrays is altered by interaction, scattering and/or absorption, with the web 102 and accordingly carries information about the uniformity or variability of fibers, moisture and other characteristics of the web 102.

Figure 3:
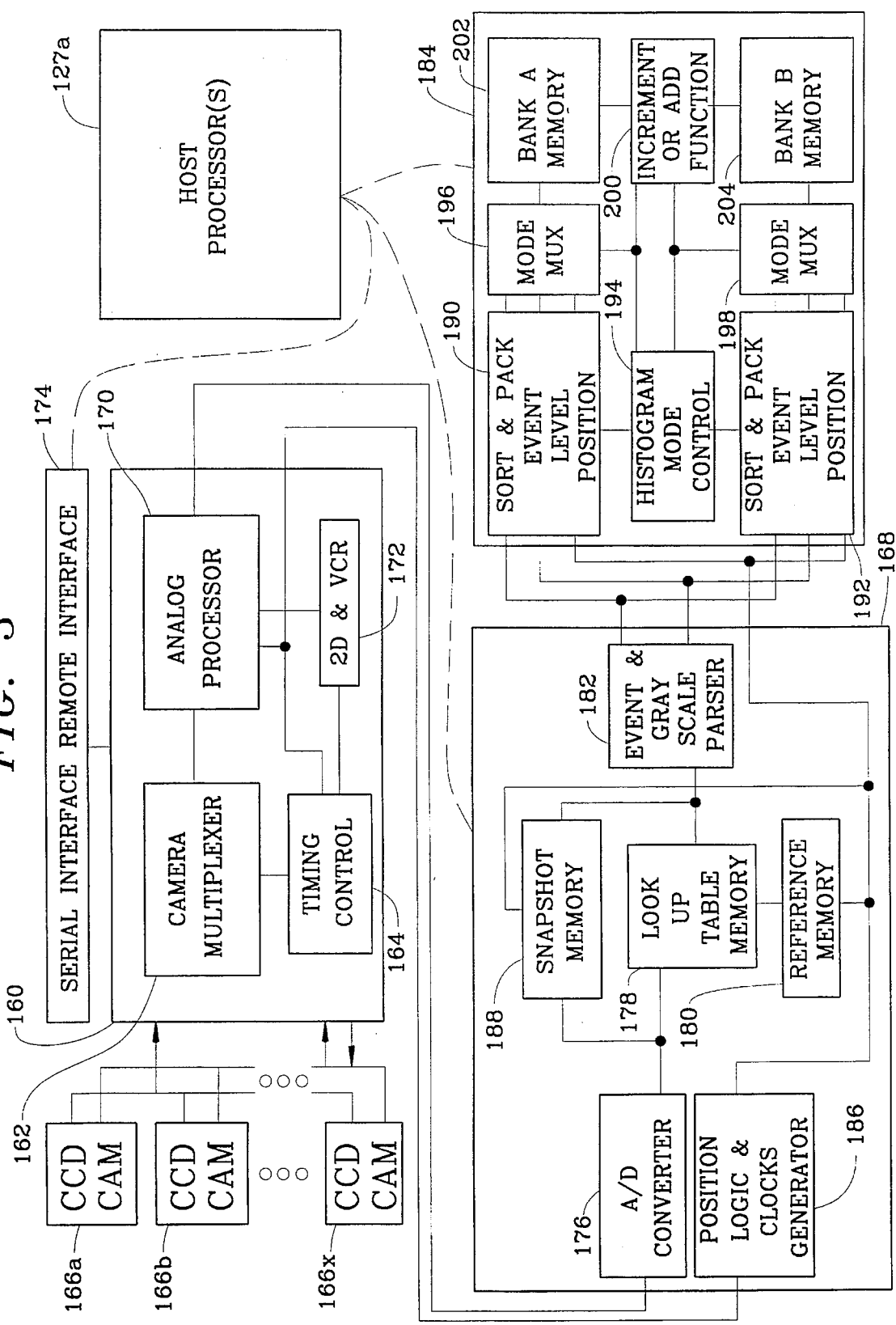
FIG. 3 is a block diagram of a system in accordance with the present invention for measuring and controlling the manufacture of sheet material.

In accordance with the present invention, the system of FIG. 3 controls the camera scans, gathers the video information from the detector arrays, and standardizes, organizes, processes, compresses, and packs the array data into terse formats suitable for control algorithm input, image presentation, and compact data feature extraction. The system can provide a multiplicity of rectangular images for differing tasks including edge-to-edge 100% sheet coverage, patch samples of microscale properties, machine direction lane samples having a width of one pixel to a selected plurality of pixels for machine health frequency analysis, selected superfine CD histories, selected actuator effect mappings, and mean and variance statistics over any selected rectangle of choice. To illustrate the operation and versatility of the system of FIG. 3, examples of measurements and machine control will now be described with reference to the digital signal processor 168 and the histogram circuit 184.

In a working embodiment of the invention of the present application, the look up table memory 178 comprises 65536=256×256 bytes. There are 8 incoming address bit lines on the left of the memory 178 in FIG. 3 which can carry 256 different codes or addresses and 8 incoming address bit lines on the bottom which can carry another 256 addresses. Thus the entire address space of the memory 178 is covered by the 16 bit address field, or rather two 8 bit subfields. In normal operation, the 8 bit lines on the left of the memory 178 are fed from the A/D converter 176 and the 8 bit lines on the bottom of the memory 178 are fed by the reference memory 180. However, it is also possible to address the look up table memory 178 directly in order to load the memory 178 with appropriate table load data from the host processor(s) 127a of the processor system 127.

For this embodiment, the reference memory 180 comprises 32768 bytes. The digital signal processor 168 sequentially selects the data to be read out from the reference memory 180 in synchronism with the digital video signals from the A/D converter 176. Thus, in normal operation, as each incoming video measurement (one or two detector responses per measurement, 1D/M or 2D/M) is A/D converted and addresses the look up table memory 178, a reference value specific to exactly that measurement and read from the reference memory 180 also addresses the look up table memory 178. The result is a look up table output byte for the i-th position measurement that is a two-variable function of two input bytes referring to the same position: look up table (LUT) memory output$_i$=f(digitized video byte$_i$, reference memory byte$_i$). This general functionality is put to specific use by the nature of the data loaded into the reference memory 180 and the look up table memory 178.

Figure 4:
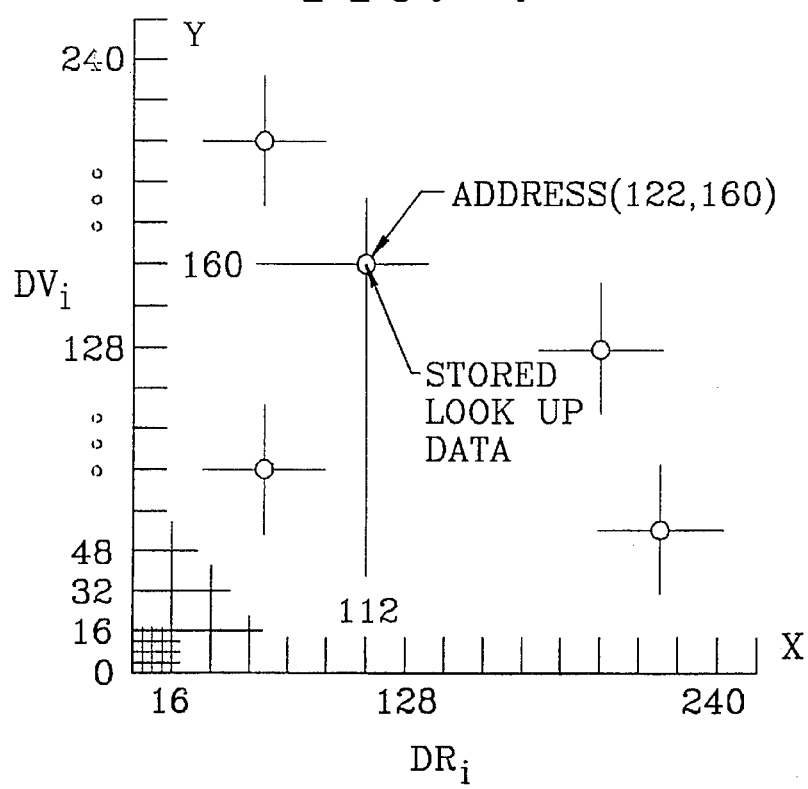
FIG. 4 is a cartesian plot representing the addressing and contents of a look up table memory of FIG. 3.

For operation of the look up table memory 178, the incoming video signal for the i-th location is digitized into one of 256 levels or codes by the A/D converter 176. The A/D converter output codes $DV_i$, represented as decimal numbers, can be viewed as y-axis tick marks or grid lines on an x-y plot with the output bytes $DR_i$ from the reference memory 180, represented as decimal numbers, being viewed as x-axis tick marks or grid lines on the x-y plot as shown in FIG. 4. For this representation, each grid intersection can be viewed as containing the output byte for the look up table memory 178 in a storage cell depicted by a circle.

The reference memory 180 output bytes generally have a relationship to standardization of the process being measured and controlled. While this is generally the case for the paper making process of FIG. 1, in contrast to a standardization of absolute sensor values to exact physical measurements, for example as used in a conventional scanning sensor, here the determination for the values contained within the reference memory 180 is more a matter of establishing normalcy. Accordingly, value selection for the contents of the reference memory 180 will be called normalization herein.

The look up table memory 178 and the reference memory 180 of the present invention can be used in a wide variety of different ways, two of which will now be described for two different measurements which can be taken on the web 102. For optical formation measurements and machine direction sampling measurements, the reference memory 180 is loaded with average response values established during scene normalization and the look up table memory 178 is loaded with event information over five or more response level zones. For optical uniformity measurements, the reference memory 180 is loaded with upper and lower limits established during scene normalization and the look up table memory 178 is loaded with both event and level information based on these limits. Each of these usages will be fully described hereinafter.

In the present invention, it is possible to store, read, sum, and average, pixel by pixel and in real time, many individual line scans of a scene that has been chosen to represent normalcy. For the hopefully bland scene of a moving paper sheet, this is nothing more than the average of a protracted look at the web 102. The average digitized optical signal value for a pixel is then stored as the reference memory byte for that pixel. A digitized normal video signal DVN for the i-th measure is:

$$DVN_i = DO_i + OAG * PN_i$$

where the subscript i denotes that all values are for the i-th measure or pixel, PN is the normal sheet physical property sensed, OAG is the overall gain from physical property value to digital byte effect, and DO is the digitized offset due to non-ideal electronics and dark pixel charge production.

Next, as regular measures stream in from post normalization image sensing the result is a digitized video signal DV of:

$$DV_i = DO_i + OAG_i (*PN_i + \Delta P_i)$$

where DO, OAG, and PN are as before and $\Delta P_i$ is the deviation of the sheet property from the normal value which causes DV to deviate from the normal value DVN. Again, this relation holds for each pixel or measurement with a possibly different gain and offset for each pixel.

The offset and overall gain may be assumed to vary slowly enough that renormalization is required only occasionally, over times on the order of tens of minutes to hours. The offset may also be assumed to be uniform for all odd pixels (A channel read out) and uniform for all even pixels (B channel readout) but slightly different between A and B channels, usually due to mismatch in the array chip charge to voltage converters and operational amplifier offsets in the camera section. The overall gain, while stable for each detector, inherently varies from detector to detector and also depends on illumination uniformity, angle to the lens centerline of the camera, and A and B channel charge to voltage converter gain mismatch. The worst part of these variations in offset and gain is that between the A and B channels which can cause "zebra striping" of results as noted earlier.

In order to eliminate the effects of gain and offset variation in the array, camera, sheet, and light source combination, the following approach is used in reference and LUT loading for optical formation and machine direction sampling. Take the ratio of the regular measure result and the normalization measure result on a measurement by-measurement basis:

$$\frac{DV_i - DO_i}{DVN_i - DO_i} = \frac{OAG_i * (PN_i + \Delta P_i)}{OAG_i * PN_i}$$

so that:

$$DV_i - DO_i = (1 + \Delta P_i/PN_i)*(DVN_i - DO_i)$$

The A/D converter 176 delivers DV, and DVN and DO are measured during normalization, DO by looking at dark reference detectors built into the detector array. The reference memory 180 is loaded with the DVN values for each pixel. The equation above is of the form:

$$y - y_o = m*(x - x_o)$$

which is a straight line having a slope of m and being offset from the origin by $(x_o, y_o)$. Comparing equations, the slope is just the fractional variation $(1+\Delta P_i/PN_i)$ from normalcy and the offset is the digitized offset $DO_i$. Plotting a set of such lines on the look up table x-y plot shown in FIG. 4 results in the graph of FIG. 5 which shows an example of a normalization response for a measure of interest of 153 A/D units while the offset is 32 A/D units. Grid crossings can be identified by deviation from the 45° "normal" line. If the regular measure came in at 153, the process would be right on normal. If the measure came in at, say 164, the process would be at (164−32)/(153−32)*100 percent or 109% or 9% above normal.

Figure 5:
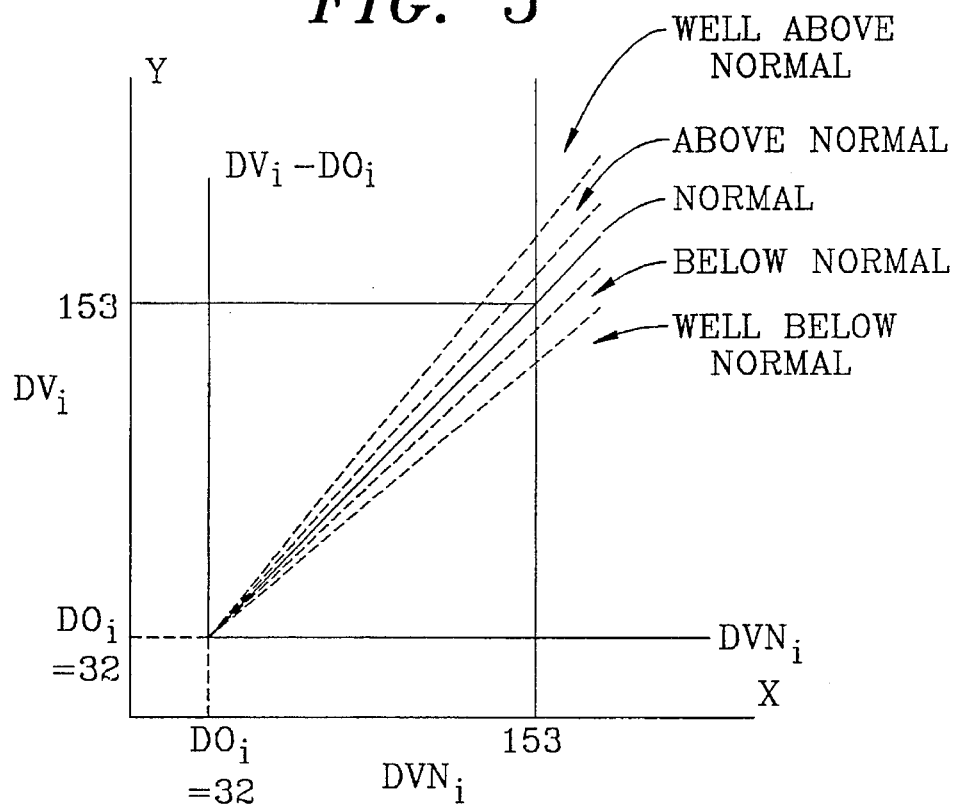
FIG. 5 illustrates a series of lines drawn on the cartesian plot of FIG. 4 segmenting measurement zones for defined web measurement limits.

The information loaded into the look up table memory 178 for formation and machine direction sampling includes codes that identify which zone the measure response is in: well above normal, above normal, normal, below normal, or well below normal, see FIG. 5. The deviation boundaries defining each of these zones may be set by the machine operator at start up or at any time thereafter and the look up table memory 178 is loaded accordingly. For example, an application may call for a ±1% normal zone, a 1% to 3% above normal zone, and a −1% to −6% below normal zone. The appropriate codes would be loaded in the appropriate zone grid point cells. It is thus apparent that the output of the look up table memory 178 is only a function of physical property deviations regardless of the individual detector gains. While five zones are illustrated, it is noted that there is considerable leeway in the coding of the zones and in how many zones are defined.

For measuring and controlling sheet uniformity, the reference memory 180 and look up table memory 178 loading is quite different. The normalization process is used to establish limits on the normal i-th measure signal excursions by setting high and low test levels and counting crossings that occur within a certain time period, for example one second, above the high level and below the low level. The high and low test levels are backed off until the counted number of crossings is acceptably low, perhaps even zero. The criteria of acceptability can be selected by the operator of the system. Such levels are determined for each one or two pixel measurement location during the normalization process.

In a working embodiment of the present invention, there are 16 choices for high level, corresponding to A/D unit levels of 0, 16, 32, 48, ..., 240 and 16 choices for low level, corresponding to 0, 16, 32, ..., 240. About half the choices are not possible, i.e. the high level is less than or equal to the low level. However, all choices where the high level is greater than the low level are reasonable. For example, suppose the measure signal for a given pixel is always found to lie within the zone from the 112 level to the 144 level, a span of 32 A/D steps or signal level bins. Then the high limit is set at 144 and the low limit is set at 112.

The loading of the reference memory 180 for each measure is a byte in which the most significant four bits code the high limit and the least significant four bits code the low limit. The codes are simply the binary coded decimal representations of the decimal limits divided by 16. Thus the 144 high limit has a code of 144/16=9 and the upper nibble of the byte is 1001. The 112 low limit has a code of 112/16=7 and the lower nibble of the byte is 0111. The load to the reference memory 180 for this measure is the byte 10010111 and means that this measure will almost always be found in the A/D unit range of 112 to 144.

Data bytes loaded into the look up table memory 178 have two parts: an upper 4 bit nibble which codes zones for identifying change of zone events and a lower 4 bit nibble which divides the span from the low limit to the high limit into 16 gray scale levels. To continue with the above example, the zone above the high limit 144, called "over", is coded by 0111. The zone from 134 (choice) to 144, called "high gray", is coded by 1011. The zone from 122 to 134, called "normal" is coded by 1111. The zone from 112 to 122 (choice), called "low gray" is coded by 1101. The zone below the low limit 112, called "under", is coded by 1110. For the gray levels, 112 and 113 are coded 0000, 114 and 115 are coded 0001, 116 and 117 are coded 0010 . . . , and 142 and 143 are coded 1111. The choice of zone boundaries between normal and high gray and between normal and low gray is arbitrary and may be selected by the operator of the system. The choice of over and under zone boundaries is also arbitrary but is preferably chosen as the high and low limits.

For every high>low limit pair, there is a look up table memory 178 byte load pattern of the same style as the example above. Thus, each incoming digitized video measurement addresses into event zones and gray scale levels of a byte load pattern in the look up table 178 which corresponds to the measurement location and is read from the reference memory 180 for that measurement location. The look up table memory 178 output byte carries information on the event zone and gray scale level, with the gray scale level being of particular benefit in terms of measurement definition if the video measurement is within the high-low limit span, i.e. in the normal zone.

Of particular significance, this information is obtained on a per-measurement (1 or 2 pixels) basis at high frequency, 10 MHz in a working embodiment, based on results of the normalization learning phase. It is noted that this form of look up table memory 178 and reference memory 180 loading can be generalized for a variety of measurements and control operations. Further, while 4 bits are utilized for the event zone and the gray scale value, it is apparent that any reasonable number of bits n could be used for these purposes or, if desired, differing numbers of bits n and m could be used for the event zone and gray scale level, respectively.

The n bit gray scale values can be stored in memory bank A 202 and memory bank B 204 of the histogram circuit 184 by performing the steps of: truncating the n lower order bits of each memory address to define spatial zones $2^n$ bits wide addressed by resulting truncated memory addresses; substituting the digital gray scale values for said truncated n lower order bits to form $2^n$ data structure addresses for each of the truncated memory addresses; addressing the memory with the data structure addresses; reading each memory location addressed by the data structure addresses; incrementing the value read from each memory location addressed by the data structure addresses; and, storing the incremented value into each memory location addressed by the data structure addresses. Accordingly, the locations addressed within each spatial zone contain not the corresponding raw pixel data but rather a count of the number of pixels within the spatial zone which were of the gray scale level corresponding to the n lower order bits of the addresses. Such data facilitates the formation of graphical gray scale representations or histogram displays and the performance of various statistical analyses.

While the operation of the look up table memory 180 and the reference memory 180 should be apparent from the foregoing description, for the sake of clarity, an example consisting of a system of 5 detector elements, numbered 1 through 5 by their comparative detector locations, will now be described. The detector element locations are used as an index into the reference memory 180 such that the current references for detector #1 are found in location #1 of the reference memory 180, similarly detector #2 references are found in address #2, and so on.

The look up table memory 178 is loaded with values such that a variable number of the digital video signals from the A/D converter 176 are mapped to the possible 16 gray scale values. The low limit value may be viewed as selecting which area of the 256 possible A/D digital video signal values are mapped to the 16 gray scale values. The difference between the high limit and the low limit defines the mapping of the range of values. This is illustrated by an excerpted portion of entries in the look up table memory 178 illustrated in FIG. 6.

Both the table entries used for reference 11-5 (high limit-low limit) and reference 10-5 (high limit-low limit) begin at A/D value 80, while the table for reference 10-4 (high limit-low limit) begins at A/D value 64. At the same time, references 11-5 and 10-4 map 6 A/D values to each gray scale value while reference 10-5 maps only 5 values to each one. In other words the low limit provides the offset while the high limit, low limit difference provides the slope of the conversion. The event data is scaled both in terms of the minimum value and the range of values mapped to the event data levels in a manner similar to the gray scale value mapping.

Given these initial conditions, the long term average for these 5 detectors is determined and is used to load the high and low limit values into the reference memory 180. For the sake of illustration, presume that it is desired to set the long term average of the detector input signal to mid scale in terms of the normalized gray scale value. Further, presume that it is desired to set the limits so that 5% of the data of the long term average is outside the range of the gray scale values.

After collecting a large number of samples, it can be determined that detectors #1 and #2 have a long term average of 125 A/D, detector #3 has a long term average of 117 A/D and detectors #4 and #5 have long term averages of 109 A/D. Using these values and a measure of the distribution of values as deviations from these averages such that the 5% value is reached sets the limit values in the reference memory 180 to: high=11 low=5 for detectors 1 and 2, i.e. memory locations 1 and 2 contain hexadecimal 0×B5 (decimal 11-5); high=10 low=5 for detector 3, i.e. memory location 3 contains hexadecimal 0×A5 (decimal 10-5); and, high=10 low=4 for detectors 4 and 5, i.e. locations 4 and 5 contain hexadecimal 0×A4 (decimal 10-4).

This selection causes the conversion of each digital video signal from the A/D converter 176 to the normalized gray scale and event values described below for each scan of the detectors 1–5. It is noted that each of the high/low limit value combinations selects a table of values as described above and shown in FIG. 6 such that there is one and only one possible result for each possible digital video signal from the A/D converter 176.

| Detector Addr | 1 | 2 | 3 | 4 | 5 |
|---|---|---|---|---|---|
| Pixel # | 1 | 2 | 3 | 4 | 5 |
| Ref's H/L | 11/5 | 11/5 | 10/5 | 10/4 | 10/4 |

The following data illustrate 5 subsequent scans of the detectors 1–5 including the digital video signal from the A/D converter 176 (A/D), the value read from the look up table memory 178 (LUT), and the data stored in the data memory, memory bank A 202 or memory bank B 204 of the histogram circuit 184, for each of the two storage modes: event level and detector address for a microscale uniformity patch mode; and, the number of occurrences of specific gray scale values for a gray scale histogram display mode.

|  |  |  |  |  |  | Data Stored |  |
|---|---|---|---|---|---|---|---|
| Scan #1 |  |  |  |  |  |  |  |
| A/D | 112 | 105 | 105 | 104 | 100 | F001 | 1–4 |
| LUT | F5 | F4 | F5 | F6 | F6 |  | 2–5's |
|  |  |  |  |  |  |  | 2–6's |
| Scan #2 |  |  |  |  |  |  |  |
| A/D | 99 | 105 | 100 | 99 | 85 | D001 | 2–3's |
| LUT | D3 | F4 | F4 | F5 | D3 | F002 | 2–4's |
|  |  |  |  |  |  | D005 | 1–5 |
| Scan #3 |  |  |  |  |  |  |  |
| A/D | 104 | 103 | 104 | 87 | 88 | F001 | 2–3's |
| LUT | F4 | D3 | F4 | D3 | F4 | D002 | 3–4's |
|  |  |  |  |  |  | F003 |  |
|  |  |  |  |  |  | D004 |  |
|  |  |  |  |  |  | F005 |  |
| Scan #4 |  |  |  |  |  |  |  |
| A/D | 97 | 134 | 147 | 162 | 154 | D001 | 1–2 |
| LUT | D2 | F9 | BD | 7F | BF | F002 | 1–9 |
|  |  |  |  |  |  | B003 | 1–D |
|  |  |  |  |  |  | 7004 | 2–F's |
|  |  |  |  |  |  | B005 |  |
| Scan #5 |  |  |  |  |  |  |  |
| A/D | 111 | 107 | 105 | 102 | 104 | F001 | 1–4 |
| LUT | F5 | F4 | F5 | F6 | F6 |  | 2–5's |
|  |  |  |  |  |  |  | 2–6's |

For the microscale uniformity patch, the results contained in memory bank A 202 or memory bank B 204 of the histogram circuit 184 from the first set listed above would be:

F001, D001, F002, D005, F001, D002, F003, D004, F005, D001, F002, B003, 7004, B005, F001.

Figures 6, 7:
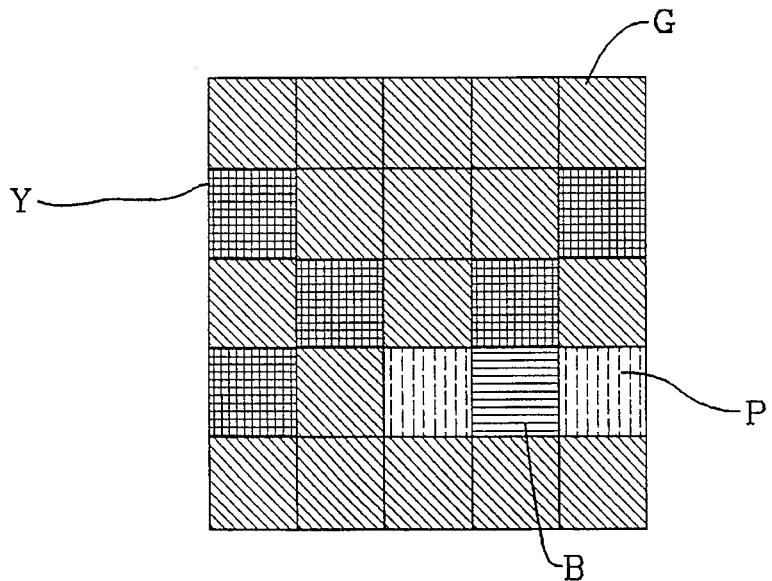
FIG. 6 is an excerpted portion of entries in a look up table memory of FIG. 3.
FIG. 7 illustrates a display of a microscale uniformity patch for data collected from 5 scans of 5 detector elements of a camera of FIG. 3.

Dividing this data by scans, substituting the colors E=Red, D=Yellow, F=Green, B=Purple, and 7=Blue, and continuing one level until a change is detected the result is a display as shown in FIG. 7 wherein:

|  | Screen Position |  |  |  |
|---|---|---|---|---|
| 1 | 2 | 3 | 4 | 5 |
| Grn | Grn | Grn | Grn | Grn |
| Yel | Grn | Grn | Grn | Yel |
| Grn | Yel | Grn | Yel | Grn |

-continued

| | | Screen Position | | |
|---|---|---|---|---|
| 1 | 2 | 3 | 4 | 5 |
| Yel Grn | Grn Grn | Pur Grn | Blu Grn | Pur Grn |

This same data is used for a machine direction variability display except that all data except that coming from detector #2, for example, is thrown away.

For the sheet uniformity profile, the results contained in the memory bank A 202 or memory bank B 204 of the histogram circuit 184 are taken from the second set listed above and would be:

| Scan Number | | Location | | | | Avg. |
|---|---|---|---|---|---|---|
| 1 | 5 | 4 | 5 | 6 | 6 | 5.2 |
| 2 | 3 | 4 | 4 | 5 | 3 | 3.8 |
| 3 | 4 | 3 | 4 | 3 | 4 | 3.6 |
| 4 | 2 | 9 | 13 | 15 | 15 | 10.8 |
| 5 | 5 | 4 | 5 | 6 | 6 | 5.2 |
| Average | | | | | | 5.7 |

Figure 8:
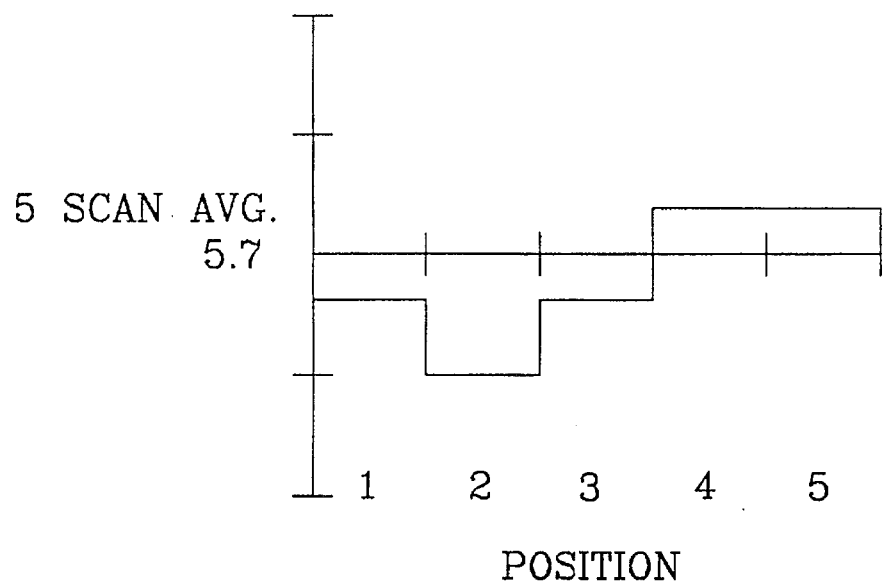
FIG. 8 is an area chart for a sheet uniformity profile.
Figure 9:
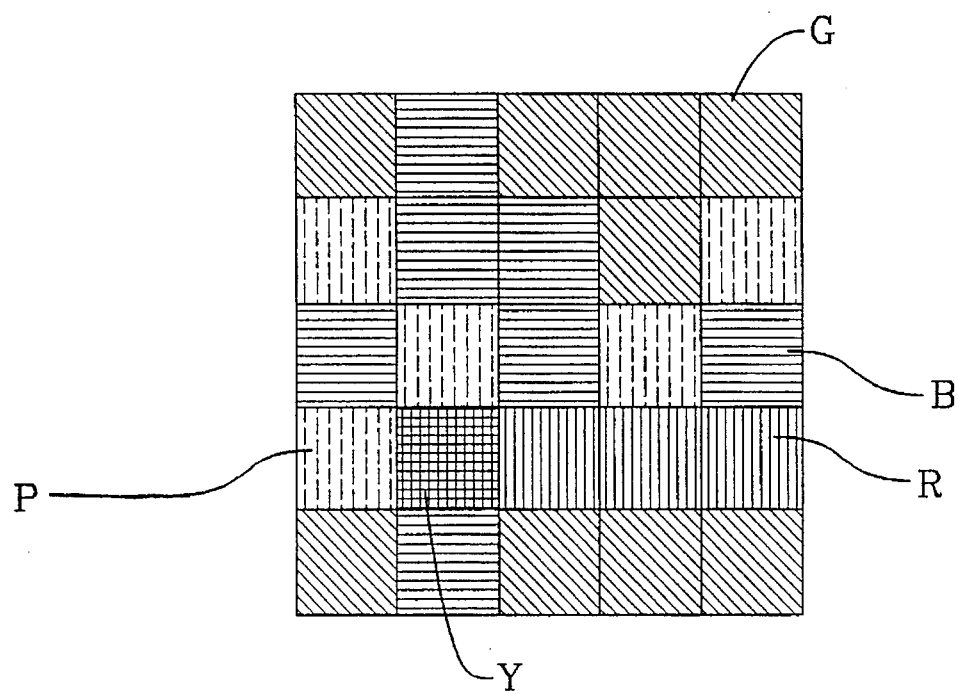
FIG. 9 is a profile history plot for data collected from 5 scans of 5 detector elements of a camera of FIG. 3.

This data is normally displayed in an area chart shown in FIG. 8 with the average value, 5.7 in the chart above, as the center line of the plot. This data can be saved as a scan profile on a scan by scan basis and can be scrolled up along with a number of others to provide a profile history plot as shown in FIG. 9 wherein zones corresponding to "average" (green), "above average" (yellow), "well above average" (red), "below average" (blue) and, "well below average" (purple) are color coded as shown. Since the distribution of values is saved at each scan, various statistical values can be calculated from these discrete points such as standard deviation, variance, etc.

By processing video signals as described, substantial amounts of data can be taken and used to display measurements of various properties and characteristics of the web 102. In this way, the web 102 can be substantially continuously monitored for measurement and control purposes even though the web may be several meters in width and traveling at speeds of 30 meters per second. If the second and third embodiments of the web sensors WS2 and WS3 are used in the present invention, even though the entire web is not monitored substantially increased numbers of web elements are monitored such that properties and characteristics of the areas of the web 102 which are not directly monitored can be estimated by interpolation. Since wide areas of the web are monitored, much more rapid evaluation of the accumulated data can be performed than is possible with conventional scanning web sensors, even with the scanning embodiment of the web sensor WS3.

The invention of the present application permits web sensing at substantially any location along the web from a wet end position occupied by the stationary web sensor 132 to the dry end of the machine substantially adjacent to the collecting reel 124. As shown in FIG. 1, a dry end sensor 210, preferably a stationary web sensor, can be used to determine an absolute value, such as the basis weight, of the web 102. Other sensors can be utilized along the web 102, for example to monitor a given process performed on the web 102. As shown in FIG. 1, the size press 120 may be monitored by sensors 212 and 214 positioned along the web 102 on opposite sides of the size press 120.

Advantageously, the stationary web sensor 132 can be utilized to measure and display the web 102 at its wet end to permit an operator of the system to evaluate one or more characteristics or properties of the web 102. For example, the uniformity of the web 102 can be monitored via the display 130 of the operator's console 126. The video signals, generated and processed as disclosed above, can also be used to control one or more characteristics and properties of the web 102. By using the signals generated by the system of the present invention for control purposes, variability in the web 102 can be substantially eliminated.

Since measurements made at the wet end of the machine can not accurately determine the ultimate product which is produced and wound onto the collecting reel 124, the absolute characteristics and properties of the web 102 cannot be assured by such control using the stationary web sensor 132. However, by utilizing any of a number of conventional control systems, variability can be substantially eliminated such that a very consistent product or web 102 is produced.

If the paper making machine 100 is initially setup to produce a known grade of paper and then operated in accordance with the present invention to produce a highly uniform product, the absolute values of the resulting paper wound onto the collecting reel 124 should be very close to the desired product. However, in accordance with the present invention, a second stationary web sensor may be provided for measuring a given characteristic of the web 102 of sheet material and generating second web signals which are representative of the web 102 in absolute terms. Such measurements may be performed by placing the second stationary web sensor adjacent to the dry end of the machine. A control system responsive to web signals from sensors at both the wet and dry ends of the machine 100 can then control the machine to maintain uniformity and an absolute value of one or more given characteristics of the web 102.

The second stationary web sensor may be the same as or similar to the web sensors described with reference to FIG. 2 above. Alternately, the second stationary web sensor may comprise weight sensing apparatus 216 for measuring the weight of the collecting reel 124 which accumulates the web 102 as it is produced. By knowing the width of the web 102 and the operating speed of the paper making machine 100, the basis weight of the web 102 can be determined from the weight of the collecting reel or, more accurately, the paper accumulated on the reel. The weight of the collecting reel 124 can be accurately determined by using conventional weight sensing devices including load cells and the like.

Having thus described the invention of the present application in detail and by reference to preferred embodiments thereof, it will be apparent that modifications and variations are possible without departing from the scope of the invention defined in the appended claims.

What is claimed is:

1. A method for measuring at least one physical property of sheet material comprising the steps of:

monitoring said sheet material at a location substantially adjacent to initial processing thereof;

generating a signal representing said sheet material adjacent to initial processing thereof;

converting said signal into digital signals having magnitudes representing monitored corresponding points on said sheet material;

addressing a reference memory in synchronism with said corresponding points on said sheet material to access point specific information for said corresponding points; and addressing a lookup table with said digital signals and said point specific information to retrieve physical property information for said sheet material corresponding to said digital signals from said lookup table.

2. A method for measuring at least one physical property of sheet material as claimed in claim 1 wherein the step of monitoring said sheet material at a location substantially adjacent to initial processing thereof is performed across the entire width of said sheet material.

3. A method for measuring at least one physical property of sheet material as claimed in claim 1 further comprising the step of storing said physical property information in a memory.

4. A method for measuring at least one physical property of sheet material as claimed in claim 3 further comprising the steps of:

processing said physical property information stored in said memory to generate image signals; and displaying said image signals.

5. A method for measuring at least one physical property of sheet material as claimed in claim 1 wherein said physical property information comprises n bit digital gray scale values and said step of storing said physical property information in memory comprises the steps of:

truncating n lower order bits of each memory address to define spatial zones $2^n$ bits wide addressed by resulting truncated memory addresses;

substituting said digital gray scale values for said truncated n lower order bits to form $2^n$ histogram addresses for each of said truncated memory addresses;

addressing said memory with said histogram addresses;

reading each memory location addressed by said histogram addresses;

incrementing the value read from each memory location addressed by said histogram addresses; and storing the incremented value into each memory location addressed by said histogram addresses.

6. A method for measuring at least one physical property of sheet material as claimed in claim 1 further comprising the step of passing said physical property information to a controller for controlling manufacture of said sheet material to maintain uniformity of said sheet material.

7. A method for measuring at least one physical property of sheet material as claimed in claim 6 further comprising the steps of:

monitoring said sheet material at a location substantially adjacent to final processing of said sheet material to generate sheet signals representative of a given characteristic of said sheet material; and controlling said machine in response to said sheet signals to further control the absolute value of said given characteristic of said sheet material.

8. A method for measuring at least one physical property of sheet material as claimed in claim 7 wherein said given characteristic comprises basis weight and the step of monitoring said sheet material at a location substantially adjacent to final processing of said sheet material comprises the step of monitoring the weight of said sheet material as it accumulates.

9. A method for measuring at least one physical property of sheet material comprising the steps of:

receiving electromagnetic radiation representative of said sheet material therefrom at a location substantially adjacent to initial processing of said sheet material;

generating a signal representing said electromagnetic radiation received from said sheet material;

converting said signal into digital signals having magnitudes representing the intensity of electromagnetic radiation received from corresponding points on said sheet material;

addressing a reference memory in synchronism with said corresponding points on said sheet material to access point specific information for said corresponding points; and addressing a lookup table with said digital signals and said point specific information to retrieve physical property information for said sheet material corresponding to said digital signals from said lookup table.

10. A method for measuring at least one physical property of sheet material as claimed in claim 9 wherein the step of receiving electromagnetic radiation representative of said sheet material therefrom is performed across the entire width of said sheet material.

11. A method for measuring at least one physical property of sheet material as claimed in claim 9 further comprising the step of storing said physical property information in a memory.

12. A method for measuring at least one physical property of sheet material as claimed in claim 11 further comprising the steps of:

processing said physical property information stored in said memory to generate image signals; and displaying said image signals.

13. A method for measuring at least one physical property of sheet material as claimed in claim 9 wherein said physical property information comprises n bit digital gray scale values and said step of storing said physical property information in memory comprises the steps of:

truncating n lower order bits of each memory address to define spatial zones $2^n$ bits wide addressed by resulting truncated memory addresses;

substituting said digital gray scale values for said truncated n lower order bits to form $2^n$ histogram addresses for each of said truncated memory addresses;

addressing said memory with said histogram addresses;

reading each memory location addressed by said histogram addresses;

incrementing the value read from each memory location addressed by said histogram addresses; and storing the incremented value into each memory location addressed by said histogram addresses.

14. A system for controlling a machine making a product in the form of a moving web of sheet material, said control system comprising:

a stationary web sensor extending across the entire width of said web of sheet material for monitoring individual elements which extend continuously across the entire width of said web of sheet material and generating web signals representative of said individual elements of said web of sheet material; and a controller responsive solely to said web signals for controlling said machine to maintain uniformity in said web of sheet material.

15. A system for controlling a machine making a product in the form of a moving web of sheet material, said control system comprising:

a scanning web sensor adapted for movement across the entire width of said web of sheet material for monitoring said web of sheet material and generating web signals representative of said web of sheet material, said scanning web sensor comprising a linear array of sensor elements aligned transverse to said web of sheet material, and said web signals being representative of individual elements of said web which correspond to individual ones of said sensor elements of said linear array; and a controller responsive to said web signals for controlling said machine to maintain uniformity in said web of sheet material.

16. A system for controlling a machine making a product in the form of a moving web of sheet material, said control system comprising:

a stationary web sensor comprising at least two linear arrays of sensor elements extending across at least two portions of said web of sheet material for monitoring said at least two portions of said web of sheet material and generating web signals representative of individual elements of said at least two portions of said web of sheet material, said individual elements corresponding to individual ones of said sensor elements of said linear arrays; and a controller responsive to said web signals for controlling said machine to maintain uniformity in said web of sheet material.

17. A system for controlling a machine making a product in the form of a moving web of sheet material, said control system comprising:

a first stationary web sensor extending across the entire width of said web of sheet material for monitoring individual elements which extend continuously across the entire width of said web of sheet material and generating first web signals representative of said individual elements of said web of sheet material;

a second stationary web sensor for measuring a given characteristic of said web of sheet material and generating second web signals representative of said web of sheet material; and a controller responsive to said first and second web signals for controlling said machine to maintain uniformity and an absolute value of said given characteristic in said web of sheet material.

18. A system for controlling a machine making a product in the form of a moving web of sheet material as claimed in claim 17 wherein said second stationary web sensor comprises weight sensing apparatus for measuring the accumulating weight of said web of sheet material as it is produced.

19. A method for controlling a machine making a product in the form of a web of sheet material, said method comprising the steps of:

initializing said machine to produce a web of sheet material having known characteristics satisfying requirements of a given product produced by said machine;

monitoring said web of sheet material at a location substantially adjacent to initial processing of said web of sheet material;

controlling said machine in response to said web signals to establish uniformity in said web of sheet material regardless of the absolute requirements of said given product;

monitoring said product at a location substantially adjacent to final processing of said web of sheet material to generate product signals representative of the weight of said product by performing the step of measuring the weight of a reel accumulating said product; and controlling said machine in response to said product signals to further control the absolute requirements of said given product.

20. A method for controlling a machine making a product in the form of a web of sheet material as claimed in claim 19 wherein the step of monitoring said web of sheet material is performed across the entire width of said web of sheet material by monitoring individual elements which extend continuously across the entire width of said web of sheet material said web signals representative of said individual elements of said web of sheet material.

21. A method for controlling at least one physical property of sheet material as said sheet material is being manufactured comprising the steps of:

positioning a first stationary sheet material sensor at a first location along said sheet material substantially adjacent to initial processing of said sheet material;

operating said first stationary sheet material sensor to generate first sensor signals representative of at least a first characteristic of discrete elements of said sheet material at said first location;

converting said first sensor signals into first digital signals having magnitudes representing said at least first characteristic of said discrete elements of said sheet material at said first location;

addressing a reference memory in synchronism with said discrete elements of said sheet material to access element specific information for said discrete elements;

addressing a lookup table with said first digital signals and said element specific information to retrieve from said lookup table physical property information for the sheet material corresponding to said first sensor signals; and controlling the manufacture of said sheet material in response to said physical property information to maintain uniformity of said at least one physical property of said sheet material.

22. A method for controlling at least one physical property of sheet material as claimed in claim 21 further comprising the steps of:

positioning a second sheet material sensor at a second location along said sheet material substantially adjacent to final processing of said sheet material;

operating said second sheet material sensor to generate second sensor signals representative of at least one physical property of said sheet material at said second location; and controlling the manufacture of said sheet material in response to said second sensor signals to maintain an absolute value of said at least one physical property of said sheet material.

23. A method for controlling at least one physical property of sheet material as claimed in claim 22 wherein the step of operating said second sheet material sensor to generate second sensor signals comprises the step of monitoring the weight of said sheet material as it accumulates.

24. A system for controlling a machine making a product in the form of a moving web of sheet material, said control system comprising:

a first stationary web sensor extending across the entire width of said web of sheet material for receiving light therefrom and generating first web signals representative of said web of sheet material;

a second stationary web sensor for measuring a given characteristic of said web of sheet material and generating second web signals representative of said web of sheet material; and a controller responsive to said first and second web signals for controlling said machine to maintain uniformity and an absolute value of said given characteristic in said web of sheet material.

25. A system for controlling a machine making a product in the form of a moving web of sheet material as claimed in claim 26 wherein said second stationary web sensor comprises weight sensing apparatus for measuring the accumulating weight of said web of sheet material as it is produced.

26. A method for controlling a machine making a product in the form of a web of sheet material, said method comprising the steps of:

initializing said machine to produce a web of sheet material having known characteristics satisfying requirements of a given product produced by said machine;

receiving light representative of said product from said web of sheet material at a location substantially adjacent to initial processing of said web of sheet material;

generating web signals in response to said light received from said web of sheet material;

controlling said machine in response to said web signals to establish uniformity in said web of sheet material regardless of the absolute requirements of said given product;

monitoring said product at a location substantially adjacent to final processing of said web of sheet material to generate product signals representative of the weight of said product by performing the step of measuring the weight of a reel accumulating said product; and controlling said machine in response to said product signals to further control the absolute requirements of said given product.

* * * * *

UNITED STATES PATENT AND TRADEMARK OFFICE
CERTIFICATE OF CORRECTION

PATENT NO. : 5,563,809
DATED : October 8, 1996
INVENTOR(S) : Williams et al.

It is certified that error appears in the above-indentified patent and that said Letters Patent is hereby corrected as shown below:

Col. 23, line 5,          "26" should read --24--.

Signed and Sealed this

Twenty-fourth Day of December, 1996

Attest:

BRUCE LEHMAN

Attesting Officer          Commissioner of Patents and Trademarks